(12) United States Patent
Redoules et al.

(10) Patent No.: US 9,181,189 B2
(45) Date of Patent: Nov. 10, 2015

(54) LIPOGENESIS INHIBITOR COMPOUNDS

(71) Applicant: PIERRE FABRE DERMO-COSMETIQUE, Boulogne-Billancourt (FR)

(72) Inventors: Daniel Redoules, Toulouse (FR); Sylvie Daunes-Marion, Toulouse (FR); Stephane Poigny, Saubens (FR); Marie-Florence Galliano, Blagnac (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/363,289

(22) PCT Filed: Dec. 10, 2012

(86) PCT No.: PCT/EP2012/074891
§ 371 (c)(1),
(2) Date: Jun. 5, 2014

(87) PCT Pub. No.: WO2013/083825
PCT Pub. Date: Jun. 13, 2013

(65) Prior Publication Data
US 2014/0315950 A1 Oct. 23, 2014

(30) Foreign Application Priority Data
Dec. 8, 2011 (FR) ...................... 11 61341

(51) Int. Cl.
C07D 211/82 (2006.01)
A61K 31/445 (2006.01)
C07D 213/80 (2006.01)

(52) U.S. Cl.
CPC ...................... *C07D 213/80* (2013.01)

(58) Field of Classification Search
None
See application file for complete search history.

(56) References Cited

U.S. PATENT DOCUMENTS

2012/0258065 A1  10/2012  Dechelette et al.

FOREIGN PATENT DOCUMENTS

EP            216290 A1    3/2010
WO    WO 2010/078393 A1    7/2010
WO    WO 2011/073370 A2    6/2011

OTHER PUBLICATIONS

Chamoin et al., "The Stille Cross Coupling Reactions on Solid Support. Link to Solution Phase Directed ortho Metalation. An Ester Linker Approach to Styryl, Biaryl and Heterobiaryl Carboxylic Acids," Tetrahedron Letters, vol. 39, 1998, pp. 4175-4178.
Cordi et al., "Synthesis of 1, 2-Diacyl-3-nicotinoyl Glycerol Derivatives and Evaluation of Their Acute Effects on Plasma Lipids in the Rat," Drug Research, vol. 45 (II), No. 9, 1995, pp. 997-1001, XP-001183487.
Fernàndez et al., "Suzuki coupling reaction for the solid-phase preparation of 5-substituted nicotinic acid derivatives," Tetrahedron Letters, vol. 46, 2005, pp. 581-585.
French Preliminary Search Report for French Application No. 1161341, dated Jul. 25, 2012.
International Search Report (Forms PCT/ISA/220 and PCT/ISA/210) for International Application No. PCT/EP2012/074891, dated Jan. 25, 2013.
Roh et al., "Multi-potentiality of a new immortalized epithelial stem cell line derived from human hair follicles," In Vitro Cellular and Developmental Biology—Animal, vol. 44, 2008 (Published online Jun. 21, 2008), pp. 236-244.
Thiboutot et al., "Activity of the Type 1 5α-Reductase Exhibits Regional Differences in Isolated Sebaceous Glands and Whole Skin," Journal of Investigative Dermatology, vol. 105, 1995, pp. 209-214.
Watanabe et al., "Studies of Hypolipidemic Agents. 1. Synthesis and Hypolipidemic Activities of Alkoxycinnamic Acid Derivatives," Journal of Medicinal Chemistry, vol. 23, 1980, pp. 50-59, XP-001007865.
Ye et al., "Effects of Topical Antiandrogen and 5-Alpha-Reductase Inhibitors on Sebaceous Glands in Male Fuzzy Rats," Skin Pharmacology, vol. 10, 1997, pp. 288-297, XP008108094.

*Primary Examiner* — Heidi Reese
(74) *Attorney, Agent, or Firm* — Birch Stewart Kolasch & Birch, LLP

(57) ABSTRACT

The present invention relates to Formula (I), wherein—if X=NH, each of $R_1$, $R_2$, $R_3$, $R_4$ represents a hydrogen atom; if X=N, the core is aromatic, and $R_2$, $R_3$ and $R_4$ represent hydrogen atoms, and R1=H, halogen, aryl, heteroaryl, alkenyl or acetylenyl; or $R_1$, $R_2$, $R_3$, $R_4$ are defined such that R1 or R2 or R3 or R4 represents a methyl group, and the three other radicals represent a hydrogen atom.

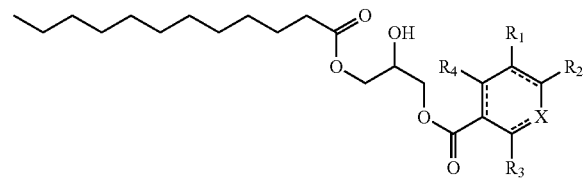

(I)

8 Claims, 1 Drawing Sheet

LIPOGENESIS INHIBITOR COMPOUNDS

Figure 1:
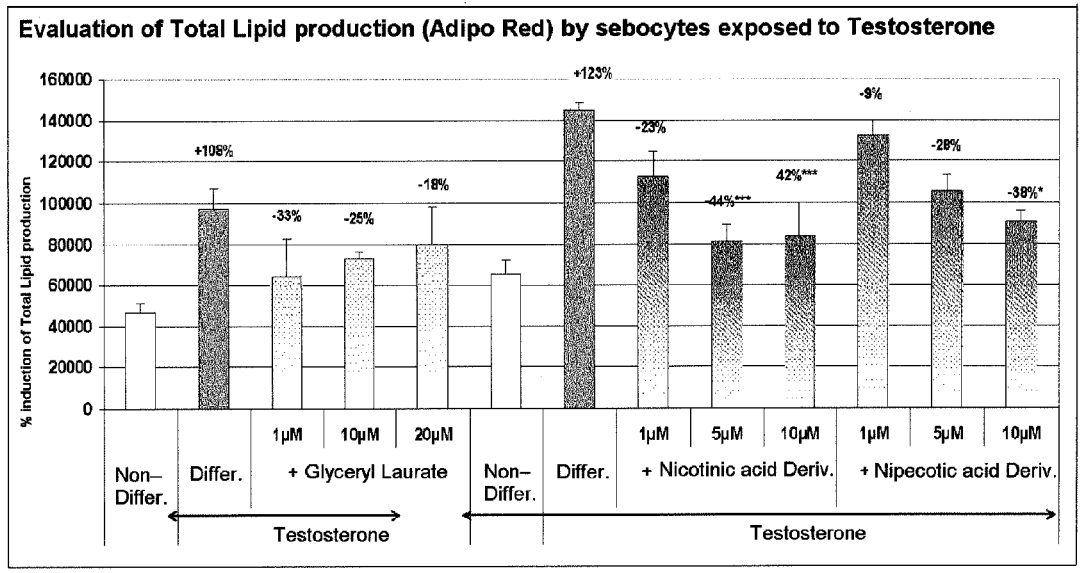

The present invention concerns novel inhibitor compounds of lipogenesis.

Seborrhoea is the excessive production of sebum by the sebaceous glands. Seborrhoea may have different causes:
- the nervous system: emotional stress, nervous tension aggravating the sebaceous function;
- fatigue;
- ill-balanced diet;
- some medications (psychotropics);
- ill-adapted cosmetic preparations <<stripping>> the skin and/or scalp and causing reaction seborrhoea;
- the main cause is of hormonal type: hyper-activation of the 5-α reductase enzyme causes seborrhoea.

The site of seborrhoea signs is the medial-facial region (forehead, nose, chin) where the sebaceous glands are the most numerous and most voluminous. Seborrhoea also occurs in the scalp where it is predominant in the frontal, frontal-temporal regions and at the top of the skull. In addition, one research study has shown that the activity of 5-α-reductase is greater in the sebaceous glands of acne-prone skin regions than in non-acne prone regions (Tiboutot et al., *J. Invest. Dermatol.*, 1995, 105: 209-14.

The sebaceous glands are clusters of specialised cells in the skin called "sebocytes".

Sebaceous secretion is the result of a multi-step process:
- production of sebum by the sebocytes during their maturation and their gradual uptake of lipid droplets;
- lysis of the sebocytes after their differentiation programme (15 days) and the release of their content, sebum, into the pilo-sebaceous channel (infundibulum);
- the rising of sebum within the infundibulum filling the latter and spreading on the surface of the stratum corneum.

Sebum is essentially formed of triglycerides (55%), wax (25%), squalene (15%) and cholesterol esters (5%).

In hyper-seborrhoea, the production of sebum becomes excessive, imparting a greasy, shiny appearance to the skin.

Also, seborrhoea is often associated with androgenic alopecia. Excess sebum may obstruct the pore of the hair bulb and thereby contribute to suffocation thereof and later to its atrophy.

In addition, hyper-seborrhoea promotes the onset of acne and seborrhoeic dermatitis. In acne, excess sebum in the hair follicle infundibulum represents a favourable environment for colonisation by *Propionibacterium acnes* and by *Malassezia* in the scalp. The onset of lesions in acne or seborrhoeic dermatitis is related to pro-inflammatory response that is too intense, via the innate immune receptors, against too high a density of *P. acnes* and *Malassezia* respectively.

All these findings allow confirmation of the advantage of associating anti-seborrhoeic activity with anti-hair loss action in a preparation intended to combat androgenic alopecia.

Similarly, the association of an anti-seborrhoeic active ingredient with an anti-acne agent allows more efficient combatting of the onset of acne lesions.

A study conducted on fibroblast cultures evidenced the inhibiting effect of glyceryl laurate (2,3-dihydroxypropyl dodecanoate) on type-1 5-α-reductase with a dose-dependent effect (WO 2011/073370). These results led to the use of glyceryl laurate in a dermocosmetic preparation to treat seborrhoea of the skin and/or scalp.

However, by solely targeting 5-α reductase, there is probably a threshold effect against the inhibited production of sebum by the sebocytes.

In the present invention the Applicant proposes novel inhibitors of lipogenesis consisting of compounds of following formula I:

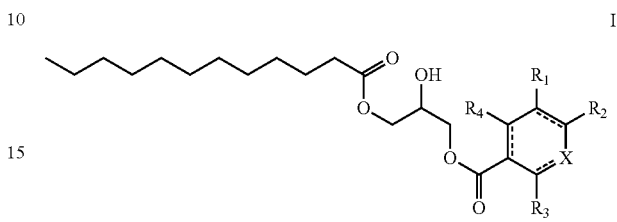

where:
- if X=NH, then each of $R_1$, $R_2$, $R_3$, $R_4$ represents a hydrogen atom;
- if X=N, then the core is aromatic and $R_1$, $R_2$, $R_3$ and $R_4$ represent hydrogen atoms, or one thereof a methyl group; and when $R_2=R_3=R_4=H$, $R_1$ may also represent a halogen atom or aryl, heteroaryl, alkenyl, acetylenyl radical.

In the present invention the different definitions of the radical $R_1$, hydrogen or methyl group, are to be interpreted as follows.

By aryl radical in the present invention is meant one or more aromatic rings each having 5 to 8 carbon atoms, possibly being attached or fused, substituted or non-substituted. In particular, the aryl groups may be phenyl or naphthyl groups and the substituents of the halogen atoms may be $C_1$ to $C_4$-alkoxy groups, $C_1$ to $C_4$-alkyl groups or the nitro group.

By heteroaryl radical in the present invention is meant an aryl radical such as previously defined in which one or more carbon atoms have been substituted by a heteroatom, for example nitrogen, oxygen or sulphur, such as pyridine, pyrimidine, imidazole, indole, furan or thiophene.

By alkenyl radical in the present invention is meant a vinyl radical substituted or not by a $C_1$ to $C_4$-alkyl radical.

By acetylenyl radical in the present invention is meant an alkynyl radical which may or may not be substituted by a $C_1$ to $C_4$-alkyl radical.

Preferably, the compounds of the invention are the following:
- glyceryl laurate-nicotinic acid: i.e. 3-(dodecanoyloxy)-2-hydroxypropyl nicotinate

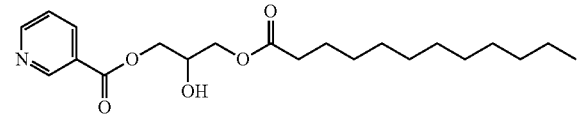 [SMILES: CCCCCCCCCCCC(=O)OCC(O)COC(=O)c1cccnc1]

or
- glyceryl laurate-nipecotic acid: i.e. 3-(dodecanoyloxy)-2-hydroxypropyl piperidine-3-carboxylate

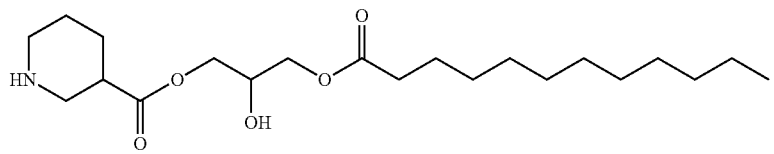 [SMILES: CCCCCCCCCCCC(=O)OCC(O)COC(=O)C1CCCNC1]

Other preferred compounds are:

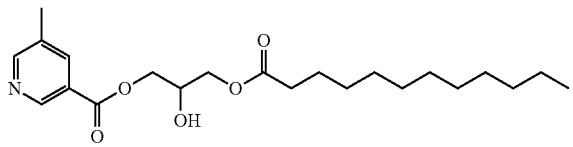 [SMILES: CCCCCCCCCCCC(=O)OCC(O)COC(=O)c1cncc(C)c1]

3-(dodecanoyloxy)-2-hydroxypropyl 5-methylnicotinate;

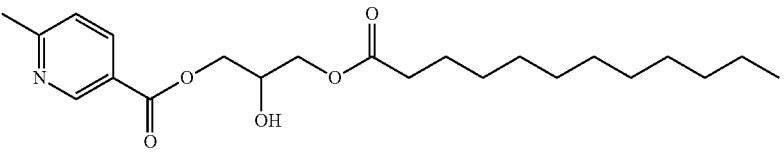 [SMILES: CCCCCCCCCCCC(=O)OCC(O)COC(=O)c1ccc(C)nc1]

3-(dodecanoyloxy)-2-hydroxypropyl 6-methylnicotinate;

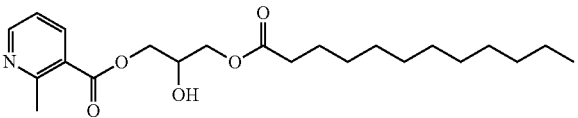 [SMILES: CCCCCCCCCCCC(=O)OCC(O)COC(=O)c1cccnc1C]

3-(dodecanoyloxy)-2-hydroxypropyl 2-methylnicotinate;

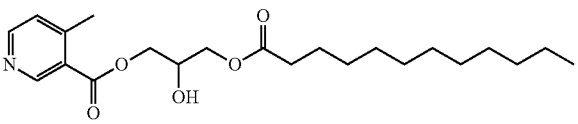 [SMILES: CCCCCCCCCCCC(=O)OCC(O)COC(=O)c1cnccc1C]

3-(dodecanoyloxy)-2-hydroxypropyl 4-methylnicotinate;

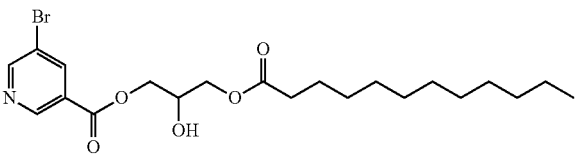 [SMILES: CCCCCCCCCCCC(=O)OCC(O)COC(=O)c1cncc(Br)c1]

3-(dodecanoyloxy)-2-hydroxypropyl 5-bromonicotinate;

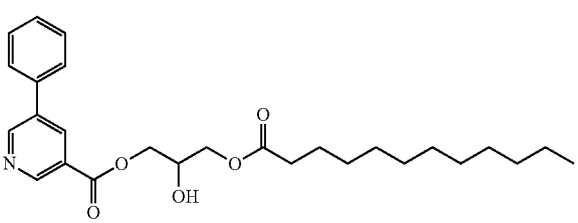 [SMILES: CCCCCCCCCCCC(=O)OCC(O)COC(=O)c1cncc(-c2ccccc2)c1]

3-(dodecanoyloxy)-2-hydroxypropyl 5-phenylnicotinate.

An example of the synthesis of 3-(dodecanoyloxy)-2-hydroxypropyl piperidine-3-carboxylate, i.e. a compound of Formula I according to the invention where X=NH and $R_1=R_2=R_3=R_4=2\times H$, is given in Example 2.

Example 1 below illustrates the general operating mode allowing the synthesis of the nicotinic derivatives of the present invention where X=N, $R_2=R_3=R_4=H$ and $R_1=H$, halogen or aryl, or $R_1$, $R_2$, $R_3$ and $R_4$ are defined such that $R_1$ or $R_2$ or $R_3$ or $R_4$ represent a methyl group, and the three other radicals represent a hydrogen atom.

The following documents *Tetrahedron Letters*, 39 (24), 4175-4178, 1998; *Tetrahedron Letters*, 46(4), 581-585, 2005; and WO 2010078393 describe inter alia the synthesis of groups such that $R_1$=heteroaryl, alkenyl, acetylenyl. The subsequent grafting of such groups on nicotinic acid allows derivatives of formula 1 of the invention to be obtained where X=N, $R_2=R_3=R_4=H$ and $R_1$=heteroaryl, alkenyl, acetylenyl.

In one particular embodiment of the invention, the formula I compounds reduce the biosynthesis of the major sebum constituents, in particular the triglyceride-forming fatty acids.

One noteworthy aspect of the compounds of the present invention is the improved bioavailability of these compounds i.e. their ability of passing through the skin to reach the sebaceous gland. Their bioavailability is improved taking into account their increase in lipophilicity: the fat-soluble ester form of the derivatives of general formula I displays better bioavailability compared with the water-soluble glyceryl laurate.

The effect of the compounds of the present invention on the regulation of sebum production was compared with that of glyceryl laurate on a sebocyte line.

Experimental conditions for sebocyte differentiation:

The Tel-E6E7 line (courtesy of Dr. Stephen Lyle, University of Massachusetts, USA) is a human epithelial line derived from stem cells of the hair follicle bulb. This line, immortalised by expression of the E6/E7 genes of HPV 16 virus, is a multi-potent epithelial line capable of differentiating into sebocytes under special culture conditions (*Multi-potentiality of a new immortalized epithelial stem cell line derived from human hair follicles*, Roh C., Roche M., Guo Z., Photopoulos C., Tao Q., Lyle S., In Vitro Cell Dev. Biol. Anim., July-August 2008, 44(7): 236-44).

Differentiation into sebocytes of the Tel-E6E7 line was conducted under the conditions described by S. Lyle. The cells were seeded in 24-well plates at a density of 25 000 cells/cm² in DME medium supplemented with 46% HamF12 medium, 6% foetal calf serum (FCII, Hyclone), 2% human serum and 10 nM EGF. Two days after seeding, the differentiation of the cells into sebocytes was induced by adding the following supplements to the culture medium: 0.1 µM testosterone (or DHT (0.1 µM)), 1 µM Troglitazone, 100 µM WyA4643 and 10 nM Insulin. The derivatives to be tested were added at the same time. Sebocyte differentiation was continued for 7 days. The culture medium and the derivatives to be tested were renewed every 2-3 days. The production of intracellular lipids was measured by quantitation of the Nile Red marker (Adipored kit, Lonza) and following the manufacturer's instructions. The amount of measured fluorescence (Relative Fluorescence Units) is proportional to the quantity of accumulated neutral intracellular lipids. All tested conditions were performed in duplicate and repeated three times.

The inventors studied the variations in lipid levels produced by the sebocytes after a differentiation time of 7 days in the presence of testosterone treated with the derivatives of the present invention.

A beneficial effect was seen to appear with the derivatives of general formula I as shown by the results obtained with nicotinic acid/glyceryl laurate conjugates in Example 1 or nipecotic acid/glycery laurate in Example 2. These results are given in appended FIG. 1 which shows the evaluation of the effect of the esters of general formula I on the production of intracellular lipids by differentiated sebocytes (Tel-E6E7 line) in the presence of testosterone and other supplements.

Figure 2:
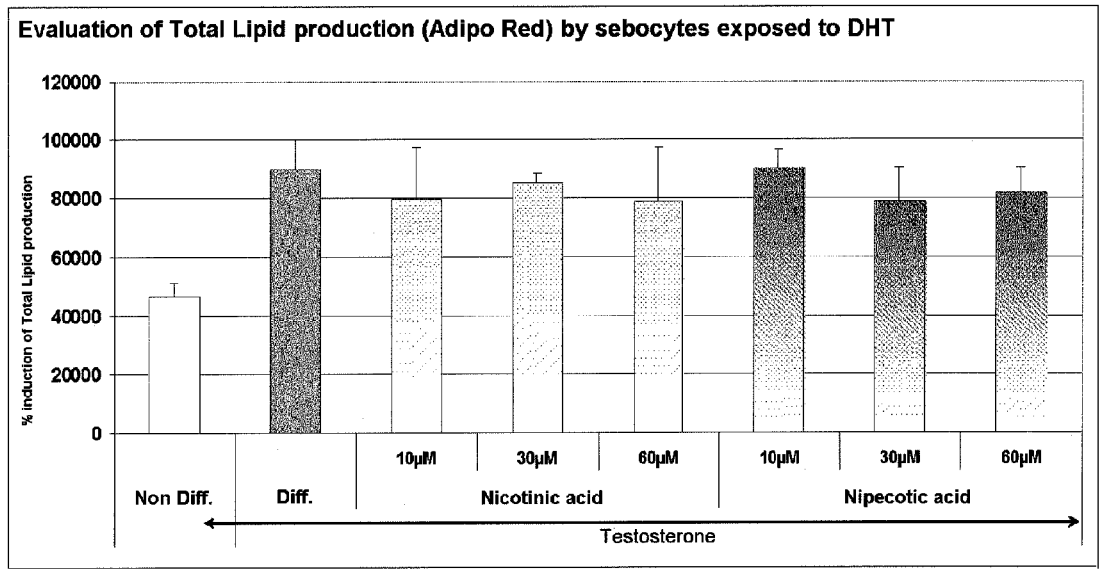

With reference to appended FIG. 1, it can effectively be seen that in the presence of glyceryl laurate nicotinate at concentrations of 5 and 10 μM the production of lipids by the sebocytes decreases most significantly. On the other hand, this trend in decrease does not reach the significance threshold when the sebocytes are treated with glyceryl laurate under the same concentration ranges. It can be noted however that a significant decrease is seen at a concentration of 10 μM for the nipecotic acid/glyceryl laurate conjugate. It can also be noted that the nicotinic or nipecotic acids do not show any inhibitor effect on lipogenesis directly induced by DHT in this model, as can be seen in appended FIG. 2 which gives the evaluation of the effect of nicotinic and nipecotic acids on the production of intracellular lipids by differentiated sebocytes (Tel-E6E7 line) in the presence of DHT and other supplements.

According to another characteristic, the invention concerns the use of a formula I compound as medication or as cosmetic active ingredient.

According to another characteristic of the invention, the medication is intended for the treatment of acne, seborrhoeic dermatitis or androgenic alopecia.

According to another characteristic the invention concerns the cosmetic use of a formula I compound for the treatment of seborrhoea.

According to another characteristic, the invention concerns a composition comprising as active ingredient an anti-seborrhoeic compound of formula I such as previously defined in association with at least one pharmaceutically or cosmetically acceptable excipient.

According to one advantageous characteristic, the invention concerns a composition for use thereof as medication.

According to another characteristic, the invention concerns a composition for use thereof to treat acne, seborrhoeic dermatitis or androgenic alopecia.

According to one particular characteristic of the invention, the formula I compounds such as previously defined are associated in said composition with at least one other active agent promoting their action in acne and androgenic alopecia indications.

In one particular embodiment of the invention, the composition intended for the treatment of acne further comprises an anti-acne active ingredient.

In another particular embodiment of the invention, the composition intended for the treatment of alopecia further comprises an anti-hair loss active agent.

According to one advantageous characteristic of the invention, it concerns the cosmetic use of a composition for the treatment of seborrhoea.

EXAMPLE 1

Nicotinic derivative ($R_1=R_2=R_3=R_4=H$), methylated nicotinic derivatives ($R_1$ or $R_2$ or $R_3$ or $R_4=CH_3$), halogenated nicotinic derivative ($R_1=Br$), nicotine derivative substituted by an unsaturated group ($R_1$=aryl).

General Operating Mode:

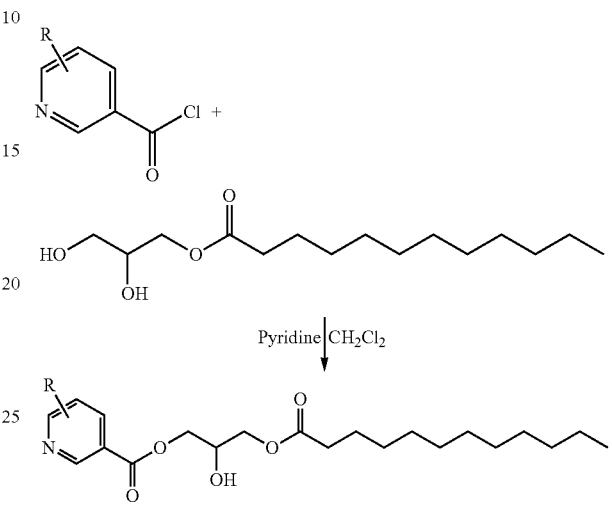

Equipment: Radley fitted with 50 ml reactors, equipped with magnetic stirring and placed in a nitrogen atmosphere.

Acyl chloride in hydrochloride form (1.5 eq) was placed in suspension in dichloromethane (20 ml per 1 g of glyceryl laurate), after which pyridine was added. After a stir time of 10 min, the glyceryl laurate (1 eq) was added to the reaction medium thus made homogeneous. The reaction medium was left under stirring at ambient temperature for 24 h. The progress of the reaction was controlled by TLC (eluent: DCM/MeOH 95:5; detection with phosphomolydic acid). The reaction medium was hydrolysed with water (10 ml per 1 g of glyceryl laurate). The organic phases were combined, washed once with water, dried over magnesium sulphate, filtered and concentrated in vacuo.

The expected esters were isolated after salification and recrystallization. For some thereof it was necessary to perform purification by silica gel chromatography.

Salification Method

The reaction mixture of bis-ester A/tri-ester B/glyceryl laurate is solubilized in ethyl ether (10 V).

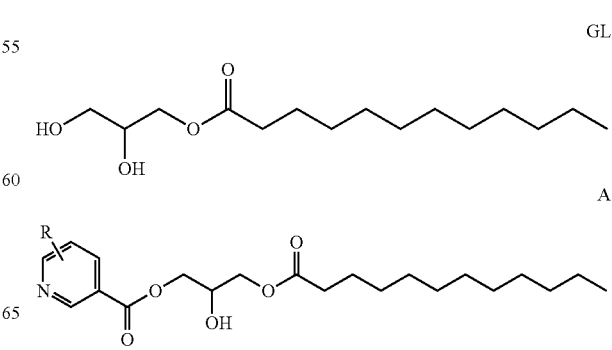

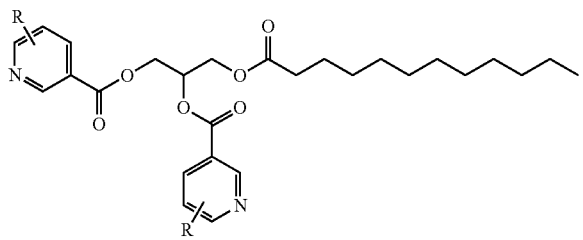

The solution was cooled over an ice bath to 0° C. in order to pour a 2N solution of hydrochloric acid in ethyl ether (3 eq). A non-filterable precipitate was formed. After stirring for 30 min the reaction medium was concentrated in vacuo to yield a white wax.

The white wax was recrystallized in acetonitrile (10 V). The white solid formed was filtered and dried in vacuo for a few hours.

The hydrochloride formed was analysed by LC-UV to determine the purity thereof. 1-nicotinoyloxy derivative of glyceryl laurate A was recrystallized to obtain purity higher than 99%.

For the nicotine derivative ($R_1=R_2=R_3=R_4=H$), synthesis was performed on a larger scale (20 g of glyceryl laurate).

Two recrystallizations made it possible to reach UV purity higher than 99%. The final compound was isolated after desalination as per the following operating mode: the hydrochloride was re-dissolved at 0° C. in a sodium hydrogen carbonate solution. The free base was extracted three times with ethyl acetate (100 ml). The combined organic phases were dried over magnesium sulphate, filtered and concentrated to yield a colourless oil which crystallizes into a white solid (9.85 g, η=35%).

For the other derivatives, synthesis was performed starting with 1 g of glyceryl laurate.

For the 2-methyl and 4-methyl derivatives, since the hydrochlorides were too soluble, the compounds were chromatographed after desalination with sodium hydrogen carbonate (Redisep Gold 40 g prepacked column, eluting conditions: dichloromethane/methanol gradient).

These mixtures obtained after chromatography were then solubilised in ethyl ether (10 V), and placed in ethyl ether (3 eq) in the presence of a 2N solution of hydrochloric acid.

Regarding the 2-methylnicotinate of 3-(dodecanoyloxy)-2-hydroxypropyl, no precipitation was observed but two phases. After decanting, the top phase was removed and concentrated (NMR analysis confirmed the majority presence of glyceryl laurate) whereas the onset of the first crystals was observed in the bottom phase. After being left overnight at ambient temperature the formed solid was recrystallized 72 h in acetonitrile (10 V). After filtering and drying in vacuo a white solid was isolated (380 mg, η=26.5%) having 88% purity.

Regarding the 4-methylnicotinate of 3-(dodecanoyloxy)-2-hydroxypropyl, a precipitate was formed in the presence of 2N hydrochloric acid solution in ethyl ether. The white solid isolated after concentration in ethyl ether was recrystallized for 48 h in acetonitrile (10 V), then filtered and dried in vacuo to yield a white solid (170 mg, η=12%) having 90% purity.

As regards the 5-bromo and 5-phenyl derivatives, a succession of recrystallization and purification operations via chromatography after desalination with sodium hydrogen carbonate (Redisep prepacked column 40 g, eluting conditions: dichloromethane/methanol gradient) allowed these compounds to be isolated in the form of a white solid having UV purity higher than 99% (5-bromo 240 mg, η=13%; 5-phenyl 160 mg, η=10%).

As regards the 5-methyl and 6-methyl derivatives, the succession of recrystallizations (one to three depending on the derivative) allowed UV purity higher than 99% to be obtained. The final compounds were then isolated after desalination using the following operating mode: the hydrochloride is re-dissolved a 0° C. in a sodium hydrogen carbonate solution. The free base is extracted three times with ethyl acetate (15 ml). The combined organic phases are dried over magnesium sulphate, filtered and concentrated to yield a white solid (5-methyl 430 mg, η=30%; 6-methyl 210 mg, η=15%).

3-(dodecanoyloxy)-2-hydroxypropyl nicotinate

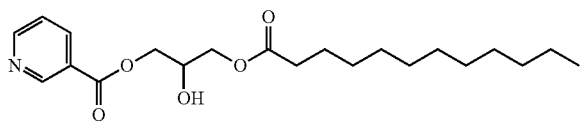 [SMILES: CCCCCCCCCCCC(=O)OCC(O)COC(=O)c1cccnc1]

$^1$H-NMR (300 MHz, CDCl$_3$): δ: 0.89 (m, 3H), 1.26 (m, 16H), 1.65 (m, 2H), 2.38 (t, 2H), 2.62 (1H), 4.28-4.48 (m, 5H), 7.45-7.48 (m, 1H), 8.34 (m, 1H), 8.81-8.82 (m, 1H), 9.27 (m, 1H).

$^{13}$C-NMR (75.5 MHz, CDCl$_3$): δ: 14.53, 23.09, 25.29, 29.52, 29.65, 29.73×2, 29.85, 29.99, 32.31, 34.51, 65.48, 66.50, 68.66, 123.98, 126.19, 138.02, 150.99, 153.70, 165.46, 174.42.

MS (ES$^+$): 380.3 [M+H]$^+$, MS (ES$^-$: 378.2 [M−H]$^-$.

Elem. An. % (C$_{21}$H$_{33}$NO$_5$): Theor. C, 66.46, H, 8.77, N, 3.69; Exp. C, 66.34, H, 8.87, N, 3.67.

3-(dodecanoyloxy)-2-hydroxypropyl 5-methylnicotinate

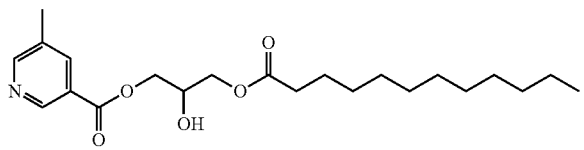 [SMILES: CCCCCCCCCCCC(=O)OCC(O)COC(=O)c1cncc(C)c1]

$^1$H-NMR (300 MHz, CDCl$_3$): δ: 0.89 (m, 3H), 1.30 (m, 16H), 1.62 (m, 2H), 2.38 (t, 2H), 2.43 (s, 3H), 4.25 (m, 3H), 4.46 (m, 2H), 8.12 (1H), 8.63 (1H), 9.05 (1H).

$^{13}$C-NMR (75.5 MHz, CDCl$_3$): δ: 14.51, 18.67, 23.07, 25.29, 29.52, 29.64, 29.72×2, 29.84, 29.99, 32.29, 34.51, 65.50, 66.47, 68.63, 125.64, 133.72, 138.03, 148.39, 154.45, 165.81, 174.39.

MS (ES$^+$): 394.1 [M+H]$^+$.

HPLC (X-bridge SM C18 column 4.6*150 mm 5 μm, H₂O_0.02% HCOOH/CH₃CN at 210 nm), Fd. 11.32 min, >99%.

Elem. An. % (C₂₂H₃₅NO₅): Theor. C, 67.15, H, 8.96, N, 3.56; Exp. C, 67.15, H, 8.96, N, 3.56.

3-(dodecanoyloxy)-2-hydroxypropyl 6-methylnicotinate

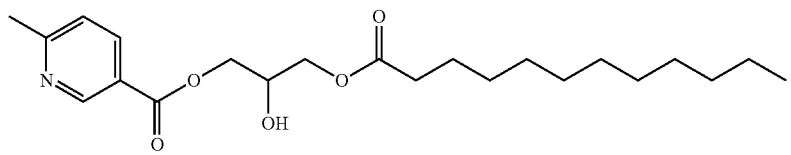 [SMILES: CCCCCCCCCCCC(=O)OCC(O)COC(=O)c1ccc(C)nc1]

¹H-NMR (300 MHz, CDCl₃): δ: 0.89 (m, 3H), 1.28 (m, 16H), 1.62 (m, 2H), 2.38 (t, 2H), 2.67 (s, 3H), 4.25 (m, 3H), 4.46 (m, 2H), 7.28 (1H), 8.20 (m, 1H), 9.13 (1H).

¹³C-NMR (75.5 MHz, CDCl₃): δ: 14.52, 23.08, 24.98, 25.29, 29.52, 29.64, 29.72×2, 29.84, 29.99, 32.30, 34.51, 65.50, 66.33, 68.77, 123.45, 123.63, 138.18, 150.59, 163.76, 166.0, 174.39.

MS (ES⁺): 394.1 [M+H]⁺.

HPLC (X-bridge SM C18 column 4.6*150 mm 5 μm, H₂O_0.02% HCO0H/CH₃CN at 210 nm), Fd. 11.27 min, >99%.

Elem. An. % (C₂₂H₃₅NO₅): Theor. C, 67.15, H, 8.96, N, 3.56; Exp. C, 65.89, H, 8.67, N, 3.44.

3-(dodecanoyloxy)-2-hydroxypropyl methylnicotinate

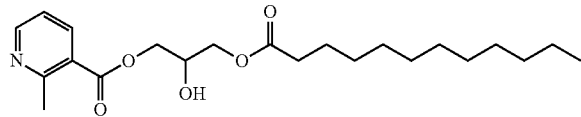 [SMILES: CCCCCCCCCCCC(=O)OCC(O)COC(=O)c1cccnc1C]

¹H-NMR (300 MHz, CDCl₃): δ: 0.89 (m, 3H), 1.27 (m, 16H), 1.63 (m, 2H), 2.37 (t, 2H), 3.24 (s, 3H), 4.25 (m, 3H), 4.53 (m, 2H), 7.9 (m, 1H), 8.8 (m, 1H), 9.01 (m, 1H).

¹³C-NMR (75.5 MHz, CDCl₃): δ: 14.03, 19.89, 22.58, 24.77, 29.03, 29.15, 29.23×2, 23.35, 29.49, 31.80, 33.99, 64.55, 67.28, 67.46, 124.18, 129.08, 143.28, 146.83, 156.6, 162.26, 173.81.

HPLC (X-bridge SM C18 column 4.6*150 mm 5 μm, NH₄COOH 10 mM pH 8 at 210 nm), Fd. 11.44 min, >88% MS (ES⁺): 394.2 [M+H]⁺.

3-(dodecanoyloxy)-2-hydroxypropyl 4 methylnicotinate

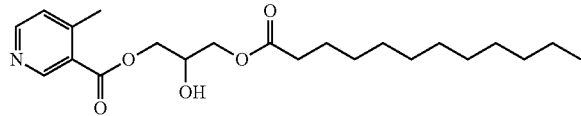 [SMILES: CCCCCCCCCCCC(=O)OCC(O)COC(=O)c1cnccc1C]

¹H-NMR (300 MHz, CDCl₃): δ: 0.89 (m, 3H), 1.28 (m, 16H), 1.64 (m, 2H), 2.37 (t, 2H), 2.96 (s, 3H), 4.25-4.52 (m, 5H), 7.83 (m, 1H), 8.8 (m, 1H), 9.87 (s, 1H).

¹³C-NMR (75.5 MHz, CDCl₃): δ: 14.53, 23.08, 23.11, 25.28, 29.55, 29.68, 29.73×2, 29.87, 30.01, 32.31, 34.52, 64.95, 67.64, 68.23, 128.89, 129.91, 142.22, 144.78, 162.13, 162.42, 174.18.

HPLC (X-bridge SM C18 column 4.6*150 mm 5 μm, NH₄COOH 10 mM pH 8 at 210 nm), Fd. 16.37 min, >90%.

MS (ES⁺): 394.2 [M+H]⁺.

3-(dodecanoyloxy)-2-hydroxypropyl 5-bromonicotinate

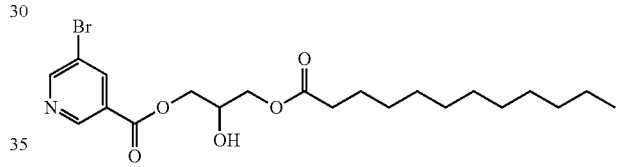

¹H-NMR (300 MHz, CDCl₃): δ: 0.89 (m, 3H), 1.27 (m, 16H), 1.63 (m, 2H), 2.39 (m, 2H), 4.25 (m, 3H), 4.47 (m, 2H), 8.46 (1H), 8.88 (1H), 9.16 (1H).

¹³C-NMR (75.5 MHz, CDCl₃): δ: 14.52, 23.08, 25.29, 29.52, 29.64, 29.72×2, 29.84, 29.99, 32.30, 34.50, 65.46, 66.71, 68.69, 110.4, 127.2, 138.18, 140.03, 149.25, 155.24, 174.39.

MS (ES⁺): 458.0 [M+H]⁺.

Elem. An. % (C₂₁H₃₂BrNO₅): Theor. C, 55.02, H, 7.04, N, 3.06; Exp. C, 55.05, H, 7.04, N, 3.06.

3-(dodecanoyloxy)-2-hydroxypropyl 5-phenylnicotinate

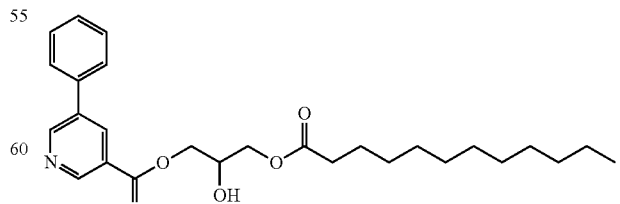

¹H-NMR (300 MHz, CDCl₃): δ: 0.89 (m, 3H), 1.27 (m, 16H), 1.65 (m, 2H), 2.38 (m, 2H), 4.30 (m, 3H), 4.52 (m, 2H), 7.47-7.64 (m, 5H), 8.50 (1H), 9.02 (1H), 9.21 (1H).

$^{13}$C-NMR (75.5 MHz, CDCl$_3$): δ: 14.53, 23.08, 25.29, 29.53, 29.65, 29.73×2, 29.85, 29.99, 32.30, 34.52, 65.49, 66.65, 68.66, 126.13, 127.62×2, 129.18, 129.70×2, 135.98, 136.76, 137.17, 149.50, 152.23, 165.61, 174.39.

MS (ES$^+$): 456.2 [M+H]$^+$.

Elem. An. % (C$_{27}$H$_{37}$NO$_5$: Theor. C, 71.18, H, 8.19, N, 3.07; Exp. C, 71.31, H, 7.95, N, 2.84.

EXAMPLE 2

3-(dodecanoyloxy)-2-hydroxypropyl piperidine-3-carboxylate

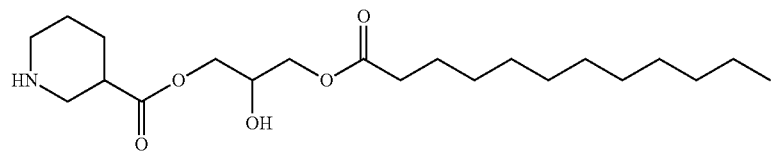 [SMILES: CCCCCCCCCCCC(=O)OCC(O)COC(=O)C1CCCNC1]

This compound was synthesized using the following reaction scheme:

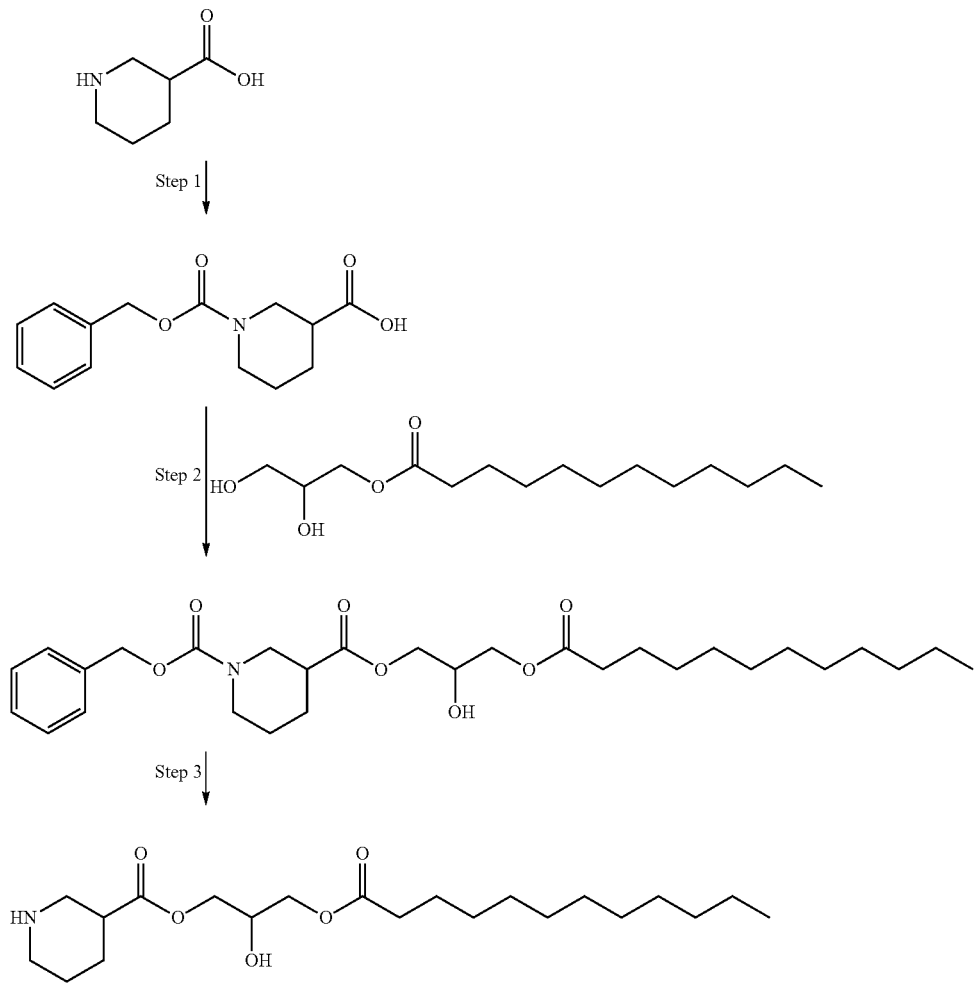

Step 1:

In a 100 ml three-necked flask, in a stream of nitrogen and under magnetic stirring the nipecotinic acid (3.7 g) was placed in solution in a 3N sodium hydroxide solution (30 ml). The solution was cooled over an ice bath to 0° C. Benzyl chloroformiate (5.8 ml) was added in fractions at 0° C. alternately with a 3N sodium hydroxide solution (9.3 ml) for a time of 45 min. After the addition time the reaction medium was pale yellow and the temperature 3° C. The ice bath was removed and the reaction medium left under stirring at ambient temperature overnight. The aqueous phase was then extracted once with ethyl ether, then acidified to pH 1 using a 3N hydrochloric acid solution. The acidified aqueous phase was extracted three times with ethyl ether. The ether extract phase was successively washed with 1N hydrochloric acid solution, then twice with saturated sodium chloride solution before being dried over magnesium sulphate, filtered then concentrated in vacuo.

The yellow oil obtained (7.35 g, 98%) was used at the following step without any purification step.

Step 2:

In a 1 l three-necked flask under a stream of nitrogen and under magnetic stirring the acid obtained at Step 1 (3.5 g) was placed in solution in dichloromethane (440 ml). EDCI.HCl (2.81 g) and DMAP (0.81 g) were added thereto. The colourless solution was left under stirring at ambient temperature for 15 min before adding glyceryl laurate (10.95 g). The reaction medium was left under stirring at ambient temperature overnight, then hydrolysed with water (200 ml). The organic phase was separated and washed twice with saturated sodium hydrogen carbonate solution then dried over magnesium sulphate, filtered and finally concentrated in vacuo to yield a white waxy solid (15.5 g).

Chromatography on a prepacked GOLD 120 g column (heptane/ethyl acetate gradient 0 to 30% in 13 column volumes (CV); heptane/ethyl acetate hold 70/30 in 5 CV) allowed separation of the expected ester from excess glyceryl laurate and the triester (3.5% detected by LCMS).

This fraction (2.64 g) was used at the following step.

Step 3:

In a 100 ml flask equipped with magnetic stirring and surmounted by a three-way stopcock (one branch connected to a nitrogen balloon, the second to a hydrogen balloon and the third to a vacuum system), the diester obtained at Step 2 (2.64 g) was placed in solution in ethyl acetate (40 ml). After two purges of the nitrogen system, palladium on carbon (0.54 g) was added to the yellow coloured solution. The reaction medium was purged three times with alternating nitrogen/vacuum, then three times with alternating hydrogen/vacuum before leaving the reaction medium under a hydrogen atmosphere. After a reaction time of 1 h 20 the reaction medium was filtered through Celite. The filtrate was concentrated in vacuo to obtain a pale yellow oil (1.88 g, total yield=17%).

$^1$H-NMR (300 MHz, CDCl$_3$): δ: 0.89 (m, 3H), 1.26 (m, 16H), 1.63 (m, 4H), 1.87 (1H), 2.36 (m, 5H), 2.60-3.06 (m, 4H), 3.74 (1H), 4.15-4.40 (m, 5H).

$^{13}$C-NMR (75.5 MHz, CDCl$_3$): δ: 14.53, 23.09, 24.8, 25.3, 27.25, 29.52, 29.65, 29.73×2, 29.85, 29.99, 32.3, 34.53, 41.88, 46.66, 48.76, 65.28, 65.30, 68.18, 174.29, 174.44.

MS (ES$^+$): 386.3 [M+H]$^+$

Elem. An. % (C$_{21}$H$_{39}$NO$_5$): Theor. C, 65.42, H, 10.20, N, 3.63; Exp. C, 65.14, H, 10.20, N, 3.56.

The invention claimed is:

1. A compound of following general formula I:

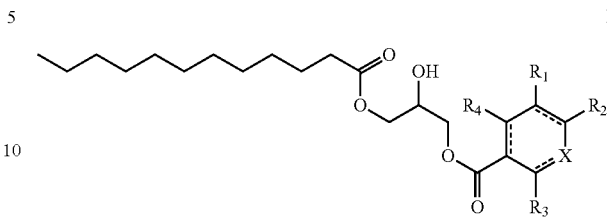

wherein
X is NH or N;
if X is NH, then each of R$_1$, R$_2$, R$_3$, R$_4$ represents a hydrogen atom;
if X is N, then the core is aromatic; and
R$_2$, R$_3$ and R$_4$ represent hydrogen atoms, and R$_1$=H, halogen, aryl, heteroaryl, alkenyl or acetylenyl;
or R$_1$, R$_2$, R$_3$, R$_4$ are defined such that R$_1$ or R$_2$ or R$_3$ or R$_4$ represent a methyl group, and the three other radicals represent a hydrogen atom.

2. A compound according to claim 1 which is 3-(dodecanoyloxy)-2-hydroxypropyl nicotinate.

3. A composition comprising as an active ingredient a compound of formula I of claim 1 together with a least one pharmaceutically or cosmetically acceptable excipient.

4. A method for treating a patient in need thereof which comprises administering to the patient a composition according to claim 3 for the treatment of seborrhoea or seborrheic conditions.

5. A composition comprising as an active ingredient the compound of claim 2 together with a least one pharmaceutically or cosmetically acceptable excipient.

6. A method for treating a patient in need thereof which comprises administering to a patient an effective amount of a compound of formula I of claim 1 for the treatment of acne, seborrheic dermatitis or androgenic alopecia.

7. A method for treating a patient in need thereof which comprises administering to a patient an effective amount of the compound of claim 2 for the treatment of acne, seborrheic dermatitis or androgenic alopecia.

8. A method for treating a patient in need thereof which comprises administering to the patient a composition according to claim 5 for the treatment of seborrhoea or seborrheic conditions.

* * * * *